(12) United States Patent
Gliner

(10) Patent No.: US 9,510,786 B2
(45) Date of Patent: Dec. 6, 2016

(54) OPTICAL PRESSURE MEASUREMENT

(75) Inventor: Vadim Gliner, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 879 days.

(21) Appl. No.: 13/166,220

(22) Filed: Jun. 22, 2011

(65) Prior Publication Data
US 2012/0330190 A1 Dec. 27, 2012

(51) Int. Cl.
*A61B 5/00* (2006.01)
*A61B 5/042* (2006.01)
*A61B 5/06* (2006.01)
*A61B 18/14* (2006.01)

(52) U.S. Cl.
CPC ........... *A61B 5/6885* (2013.01); *A61B 5/6852* (2013.01); *A61B 5/6869* (2013.01); *A61B 90/06* (2016.02); *A61B 5/042* (2013.01); *A61B 5/062* (2013.01); *A61B 5/063* (2013.01); *A61B 5/6856* (2013.01); *A61B 18/1492* (2013.01); *A61B 2090/065* (2016.02); *A61B 2562/0233* (2013.01); *A61B 2562/0247* (2013.01)

(58) Field of Classification Search
CPC ...... A61B 2019/464–2019/466; A61B 5/6885; A61B 2018/2255; A61B 2018/2261; A61B 2018/2266; A61B 2018/2288; A61B 2562/0247; G04L 19/0076–19/0079
USPC ................................................. 600/561, 587
See application file for complete search history.

(56) References Cited

U.S. PATENT DOCUMENTS

| | | | |
|---|---|---|---|
| 5,325,865 A | 7/1994 | Beckman et al. | |
| 6,506,313 B1* | 1/2003 | Fetterman et al. | 216/24 |
| 7,689,071 B2* | 3/2010 | Belleville et al. | 385/13 |
| 8,567,265 B2 | 10/2013 | Aeby et al. | |
| 2002/0183597 A1 | 12/2002 | Kaufman et al. | |
| 2004/0031326 A1* | 2/2004 | Lenzing et al. | 73/800 |
| 2004/0254438 A1 | 12/2004 | Chuck et al. | |
| 2005/0041905 A1* | 2/2005 | Lagakos et al. | 385/12 |
| 2008/0275428 A1 | 11/2008 | Tegg | |

(Continued)

FOREIGN PATENT DOCUMENTS

| | | | |
|---|---|---|---|
| CN | 101132730 | 2/2008 | |
| DE | 10 335 313 A1 | 3/2005 | |
| WO | WO 2005011511 A1 * | 2/2005 | A61B 19/00 |

OTHER PUBLICATIONS

European Patent Office machine translation from German to English of DE 103 35 5313 A1. Accessed on Nov. 29, 2013.*

(Continued)

*Primary Examiner* — Adam J Eiseman

(57) ABSTRACT

Sensing apparatus, consisting of a housing, including a medium having an elastic, transparent outer surface configured to contact a tissue within a living body and to deform in response to a force exerted by the body tissue on the surface. The apparatus has a radiation source contained in the housing and configured to direct radiation toward the surface, as well as a radiation detector contained in the housing and configured to sense the radiation that is reflected from the surface and to output a signal indicative of an amplitude of the reflected radiation. The apparatus further has a processor, which is coupled to measure a change in the signal due to deformation of the surface and, responsively to the change, to output an indication of the force.

13 Claims, 4 Drawing Sheets

(56) References Cited

U.S. PATENT DOCUMENTS

2009/0326390 A1* 12/2009 Belalcazar ......... A61B 5/02154
600/486
2010/0094163 A1 4/2010 Deladi

OTHER PUBLICATIONS

U.S. Appl. No. 12/938,458, filed Nov. 3, 2010.
European Search Report Appln No. 12 17 2882 dated Sep. 27, 2012.

* cited by examiner

OPTICAL PRESSURE MEASUREMENT

FIELD OF THE INVENTION

The present invention relates generally to force or pressure measurement, and specifically to such measurement using an optical system.

BACKGROUND OF THE INVENTION

Medical probes are known that incorporate a force or pressure measurement system. Such measurements may be used during the course of a medical procedure to provide information as to the progress of the procedure. During an ablation procedure, for example, it may be advantageous to know the force applied to tissue being ablated.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides sensing apparatus, including:

a housing, including a medium having an elastic, transparent outer surface configured to contact a tissue within a living body and to deform in response to a force exerted by the body tissue on the surface;

a radiation source contained in the housing and configured to direct radiation toward the surface;

a radiation detector contained in the housing and configured to sense the radiation that is reflected from the surface and to output a signal indicative of an amplitude of the reflected radiation; and a processor, which is coupled to measure a change in the signal due to deformation of the surface and, responsively to the change, to output an indication of the force.

Typically the medium consists of an elastic transparent solid. The solid may have a further outer surface opposite the elastic outer surface. The radiation source may be fixedly mounted on the further outer surface. Alternatively, the apparatus includes a radiation guide which couples the radiation source to the further outer surface. The radiation detector may be fixedly mounted on the further outer surface. Alternatively, a radiation guide may couple the radiation detector to the further outer surface.

In a disclosed embodiment the housing includes an external wall of a catheter probe.

In a further disclosed embodiment the elastic, transparent outer surface is convex.

In a yet further disclosed embodiment the processor includes a memory storing a calibration relation between the force and the change in the signal, and the processor is configured to compare a further change in the signal with the calibration relation to output a value of a further force exerted by the body tissue on the surface.

There is also provided, according to an embodiment of the present invention, sensing apparatus, including:

an elastic transparent medium having a first outer surface configured to contact a tissue within a living body and to deform in response to a force exerted by the tissue on the first outer surface;

a radiation source coupled to a second outer surface of the medium and configured to direct radiation toward the first outer surface;

a radiation detector coupled to the second outer surface of the medium and configured to sense the radiation that is reflected from the first outer surface and to output a signal indicative of an amplitude of the reflected radiation; and a processor, which is coupled to measure a change in the signal due to deformation of the first outer surface and, responsively to the change, to output an indication of the force.

The radiation source may be fixedly mounted on the second outer surface. The radiation detector may also be fixedly mounted on the second outer surface.

There is further provided, according to an embodiment of the present invention, a method for sensing force, including:

attaching a medium to a housing, the medium having an elastic, transparent outer surface configured to contact a tissue within a living body and to deform in response to a force exerted by the body tissue on the surface;

directing radiation toward the surface from a radiation source contained in the housing;

sensing the radiation that is reflected from the surface with a radiation detector contained in the housing;

outputting a signal indicative of an amplitude of the reflected radiation;

measuring a change in the signal due to deformation of the surface: and responsively to the change, outputting an indication of the force.

There is further provided, by an embodiment of the present invention, a method for sensing force, including:

providing an elastic transparent medium having a first outer surface configured to contact a tissue within a living body and to deform in response to a force exerted by the tissue on the first outer surface;

coupling a radiation source to a second outer surface of the medium;

configuring the radiation source to direct radiation toward the first outer surface;

coupling a radiation detector to the second outer surface of the medium;

sensing with the radiation detector the radiation that is reflected from the first outer surface;

outputting from the radiation detector a signal indicative of an amplitude of the reflected radiation;

measuring a change in the signal due to deformation of the first outer surface; and responsively to the change, outputting an indication of the force.

The present disclosure will be more fully understood from the following detailed description of the embodiments thereof, taken together with the drawings, in which:

DETAILED DESCRIPTION OF EMBODIMENTS

Overview

An embodiment of the present invention provides a force sensor which may be incorporated into a catheter probe. The sensor comprises a radiation source, typically an LED (light emitting diode), and a detector of the radiation. The detector may typically be a photo-diode or a photo-transistor. The sensor also comprises a medium having an elastic, transparent outer surface configured to contact body tissue and to deform in response to a force exerted by the tissue on the surface. The medium is typically in the form of a transparent lens, and the outer surface is typically curved. The medium, the radiation source, and the radiation detector may be mounted in a housing, which typically comprises the external wall of a catheter probe.

The radiation source is configured to direct its radiation towards the outer surface. The radiation detector is configured to sense radiation reflected from the surface, and to output a signal in response to a level or an amplitude of the reflected radiation. Typically, the radiation source and radiation detector are mounted on a surface of the medium opposite to the transparent outer surface.

A processor measures a change in the signal due to deformation of the outer surface, and is able to formulate a value of the force deforming the surface as a function of the change.

Embodiments of the present invention provide a simple, small, low-cost sensor that may be advantageously incorporated into the distal tip of a probe.

System Description

Figure 1:
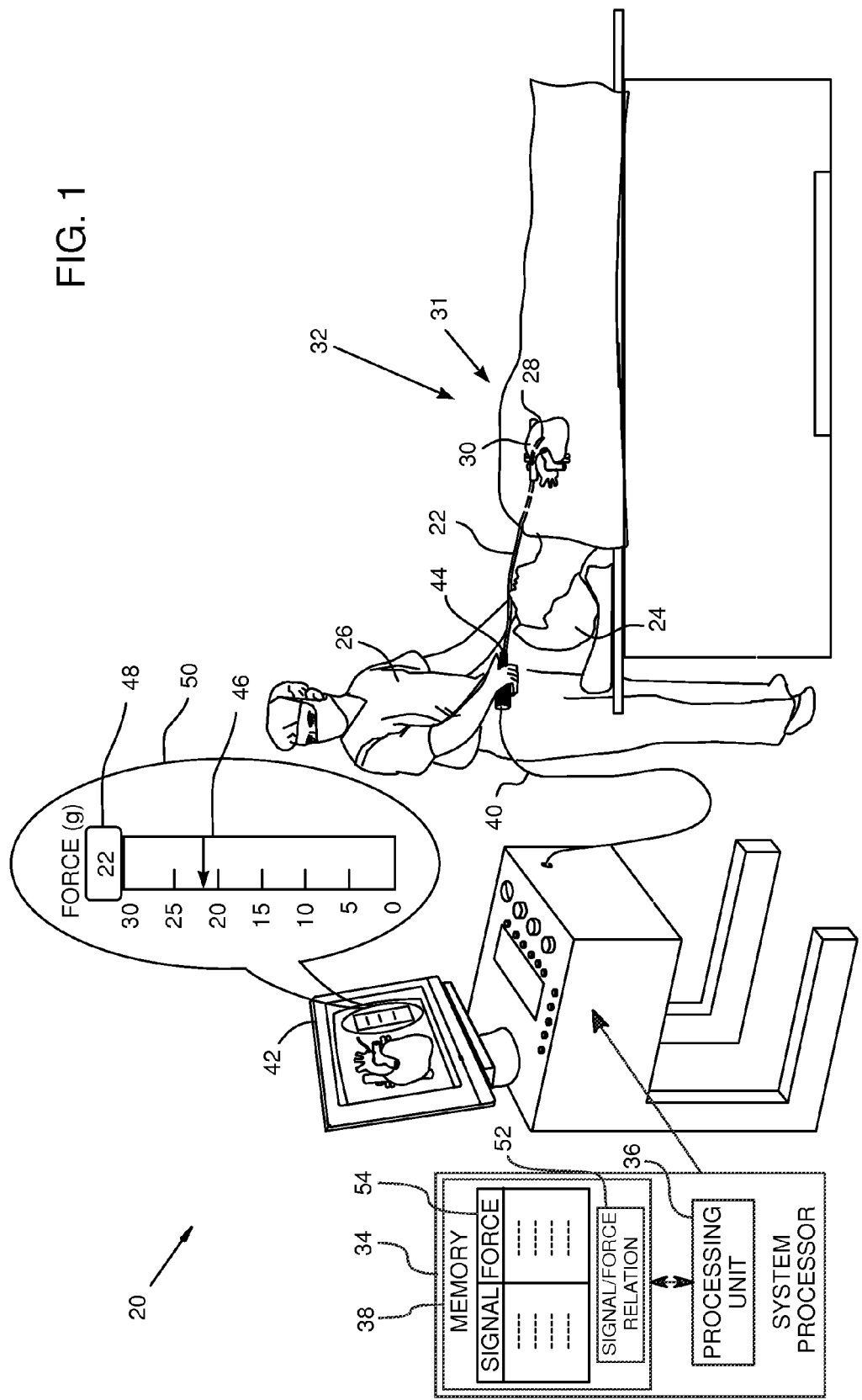
FIG. 1 is a schematic illustration of a system for measuring force exerted by a probe, according to an embodiment of the present invention.

Reference is now made to FIG. 1, which is a schematic illustration of a system 20 for measuring force exerted by a probe, according to an embodiment of the present invention. System 20 comprises a catheter probe 22 which is inserted into the body of a patient 24 during a medical procedure. Probe 22 comprises any catheter probe known in the art, such as a generally linear probe, or a "lasso" probe produced by Biosense Webster of Diamond Bar, Calif. The procedure is performed by an operator 26, typically a medical professional. By way of example, the procedure assumed in the description herein comprises insertion of a distal tip 28 of the probe into a heart 30 of the patient. However, it will be understood that embodiments of the present invention are not limited to such a procedure, but rather may be used for any procedure requiring or using knowledge of the force exerted by a probe.

Distal tip 28 of the probe comprises an optical pressure sensor 32, which is able to measure force exerted by the distal tip on body tissue 31 that is contacted by the distal tip. By way of example, tissue 31 is assumed to comprise tissue of heart 30. The construction and operation of sensor 32 is described in more detail below.

Probe 22 typically also comprises tracking elements in distal tip 28 which enable system 20 to track the position and orientation of the distal tip. For example, the position and orientation may be measured using coils in the distal tip which detect levels of magnetic fields generated by magnetic field transmitters external to patient 24. Such a technique for measuring the position and location of the distal tip is used in Carto system probes produced by Biosense Webster. Other techniques for tracking the position and orientation of the distal tip, such as by using impedance measurements between electrodes on the distal tip and one or more electrodes on the skin of patient 24, are known in the art. System 20 is assumed to use one or more of these techniques in order to measure the position and orientation of distal tip 28. For simplicity and clarity, tracking elements within the distal tip that are used to track the position and orientation are not shown in the diagram. In addition, other elements of distal tip 28, such as electrodes that may be used for electrophysiological measurements and/or for ablating body tissue of patient 24, are not shown in the diagram.

Signals from the tracking elements are processed by a system processor 34, comprising a processing unit 36 communicating with a memory 38. The signals transfer via a cable 40, connecting the tracking elements of probe 22, as well as other elements of the probe such as electrodes incorporated in the distal tip, to the processor. The processor, under overall control of operator 26, uses software stored in memory 38 for analyzing the signals from the tracking elements, as well as to perform other functions related to the operation of system 20. Results of the operations performed by processor 34 are presented to the operator on a screen 42, which typically displays a graphic user interface to the operator, and/or an image of heart 30. The software may be downloaded to processor 34 in electronic form, over a network, for example, or it may, alternatively or additionally, be provided and/or stored on non-transitory tangible media, such as magnetic, optical, or electronic memory.

Probe 22 is typically controlled by a probe manipulator 44 which is mechanically connected to the proximal end of the probe. Operator 26 holds the manipulator and uses it in order to manage entry and exit of the probe into and out of the patient.

A level of the force measured by sensor 32 may be presented to operator 26 on screen 42, in an analog form 46 and/or in a digital form 48, as illustrated by a magnified section 50 of FIG. 1. Alternatively or additionally, the force value determined by sensor 32 may be used by processor 34 in determining other factors related to the procedure being performed by the operator, for instance in determining a quality of contact of distal tip 28 with tissue of heart 30. The processor typically evaluates the force measured by the sensor using a sensor signal/force calibration relation 52, derived from a lookup table 54 stored in memory 38. The formulation and use of relation 52, and generation of table 54, are described below.

Figure 4:
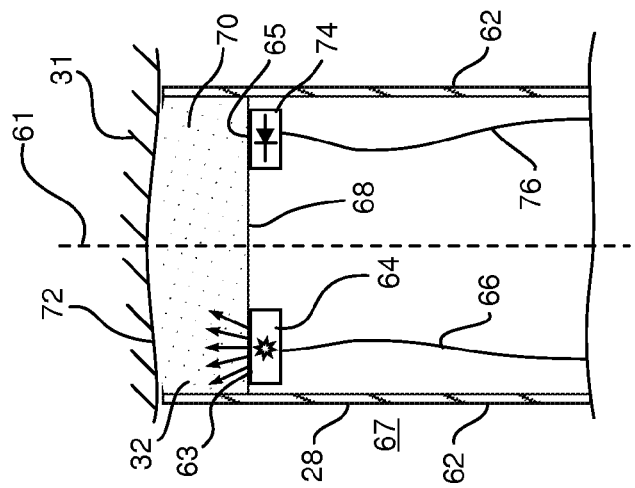
FIGS. 2, 3, and 4 are schematic cross-sections of a sensor in the probe, according to embodiments of the present invention.
Figure 3:
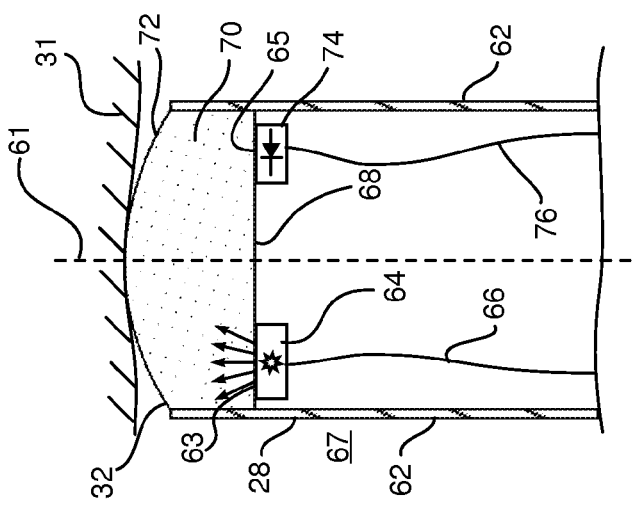
Figure 2:
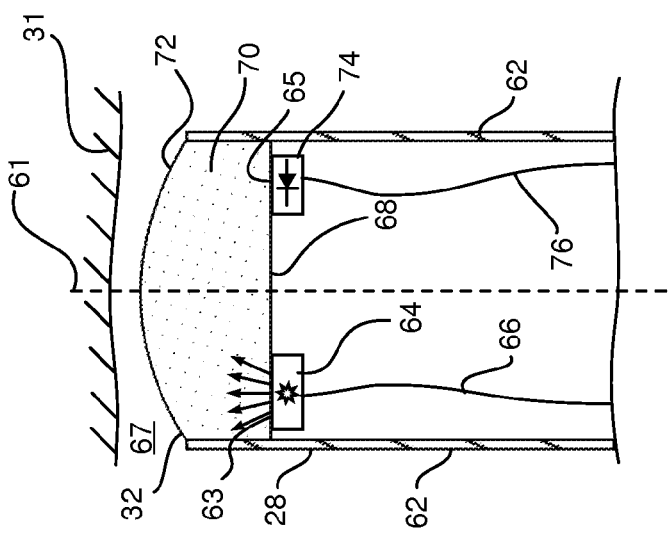

FIGS. 2, 3 and 4 are schematic cross-sections of sensor 32, according to embodiments of the present invention. Sensor 32 is assumed to be in proximity to body tissue 31, and the sensor measures the force exerted by the body tissue on the sensor (which equals the countervailing force exerted by the sensor on the body tissue) when the sensor contacts the tissue. FIG. 2 illustrates a cross-section of the sensor when it is close to, but not in contact with tissue 31. FIG. 3 illustrates a cross-section of the sensor when it exerts a low level force on the body tissue, such as when the sensor has just contacted the tissue. FIG. 4 illustrates a cross-section of the sensor when the force between sensor 32 and body tissue 31 is a high level. For clarity in the following description of elements of sensor 32, distal tip 28 is assumed to be substantially cylindrical, having an axis of symmetry 61. Distal tip 28 may be assumed to be surrounded by a fluid 67, which is typically blood or a mixture of blood and other fluids present during the medical procedure for which probe 22 is being used.

Sensor 32 is mounted within a housing 62, herein assumed to comprise the external tubing wall of probe 22. Housing 62 is also referred to herein as tubing wall 62, or wall 62. Sensor 32 uses a radiation source 64 which typically comprises a light emitting diode (LED) able to emit electromagnetic radiation. Alternatively, source 64 may comprise another type of radiation emitter known in the art, such as a laser, an incandescent source or a gas discharge tube. The radiation source may be powered from processor 34 via cabling 66. Source 64 is coupled to an elastic transparent solid medium 70, typically by being mounted using optical cement onto a first surface 68 of the medium, as is illustrated in the figures. Source 64 may be mounted on a region 63 of surface 68 close to wall 62, away from axis 61. Region 63 thus acts as an inlet port of medium 70, for the radiation from source 64. For clarity in the description herein, by way of example, region 63 is assumed to be left of axis of symmetry 61.

Alternatively, radiation source 64 may be coupled by a radiation transmitting cable or waveguide, such as a fiber optic cable, to region 63. In this case source 64 may be located at the proximal end of probe 22.

The radiation emitted by source 64 is typically visible radiation. However, there is no requirement that the radiation is in the visible spectrum, and it may be in the infra-red, ultra-violet, or other region of the electromagnetic spectrum.

Medium 70 is in the general form of a lens, and the medium is also referred to herein as lens 70. In lens 70, first surface 68 is typically generally flat, and the medium is oriented so that surface 68 is towards the proximal end of probe 22. A second surface 72 of lens 70, opposite the first surface, is typically approximately convex and protrudes from the distal end of probe 22, i.e., from distal tip 28. Lens 70 typically has an axis of symmetry that is congruent with axis 61. Medium 70 is selected to be transparent to the radiation emitted from source 64.

Also coupled to surface 68 is a radiation detector 74, which is configured to convey an electrical output signal, via cabling 76, to processor 34, on receipt of reflected radiation that originates in source 64. The signal is a measure of the level i.e., the amplitude, of the reflected radiation. Typically, detector 74 comprises a photodiode or a photo-transistor, in which case the device may be powered, if required, by processor 34 via cabling 76. Detector 74 may be mounted on a region 65 of surface 68 close to wall 62 away from axis 61. Region 65 thus acts as an exit port for the radiation from source 64. Regions 63 and 65 are on opposite sides of axis 61, and are typically approximately equidistant from the axis. Following on from the exemplary description of the location of region 63 above, region 65 is to the right of axis 61.

Alternatively, detector 74 may be coupled via a radiation transmitting cable or waveguide, such as a fiber optic cable, to region 65. In this case detector 74 may be located at the proximal end of probe 22.

In a disclosed embodiment, medium 70 is formed as a coextrusion of a blend of thermoplastic polyurethanes, having a thickness of approximately 125 microns. By way of example, source 64 may be an infra-red LED emitting radiation with a peak wavelength of approximately 870 nm, such as the CN870-30P LED produced by Marubeni America Corporation of Santa Clara, Calif., which is approximately 0.3 mm square. Source 64 is mounted directly on surface 68 of medium 70. Also by way of example, detector 74 may be a silicon NPN phototransistor, such as the T1090P phototransistor produced by Vishay Semiconductors of Shelton, Conn., which is approximately 0.5 mm square. Detector 74 is also mounted directly on surface 68.

When sensor 32 operates, radiation from source 64 enters medium 70, and strikes surface 72. At surface 72, the incident radiation typically partially transmits through the surface, and partially reflects from the surface. Some of the partially reflected radiation returns to detector 74, which generates a signal according to the level of radiation received by the detector.

The level of radiation received at detector 74 depends on a number of factors, including:
  the intensity and spatial distribution of the radiation entering region 63 from source 64;
  the transmissivity of medium 70;
  the angles made by the different sections of surface 72 with radiation incident on the sections; and
  whether the different sections are in contact with body tissue 31.

It will be understood that the factors are listed in the above order only for convenience in referring to them in the present description, and the order is not material to embodiments of the present invention.

During the medical procedure in which sensor 32 is used, the first two factors in the list are typically invariant with respect to changes in the force acting between the sensor and body tissue 31. However, the second two factors, i.e. the angles made by the different sections of surface 72, and whether a section is in contact with body tissue, do change with changes in the force.

Because medium 70 is elastic, contact with tissue 31, creating a force from the tissue on the medium, causes deformation of surface 72, the deformation comprising a change in the curvature of surface 72. The deformation changes the angles made by the different sections of surface 72 with radiation incident from region 73.

In addition, because of the elasticities of medium and tissue 31, as the force between the two media changes, the area of the tissue in contact with surface 72 also changes. The change in area of contact influences the radiation returning to detector 74 from surface 72, because of factors such as the transmissivity and refractive index of fluid 67, and the transmissivity and refractive index of tissue 31.

In consequence of the effects caused by the last two factors, embodiments of the present invention are able to use a level of radiation received by detector 74 as a good measure of the force acting between medium 70 and tissue 31, when the two media are in contact. A calibration process for sensor 32 is described below.

Figure 5:
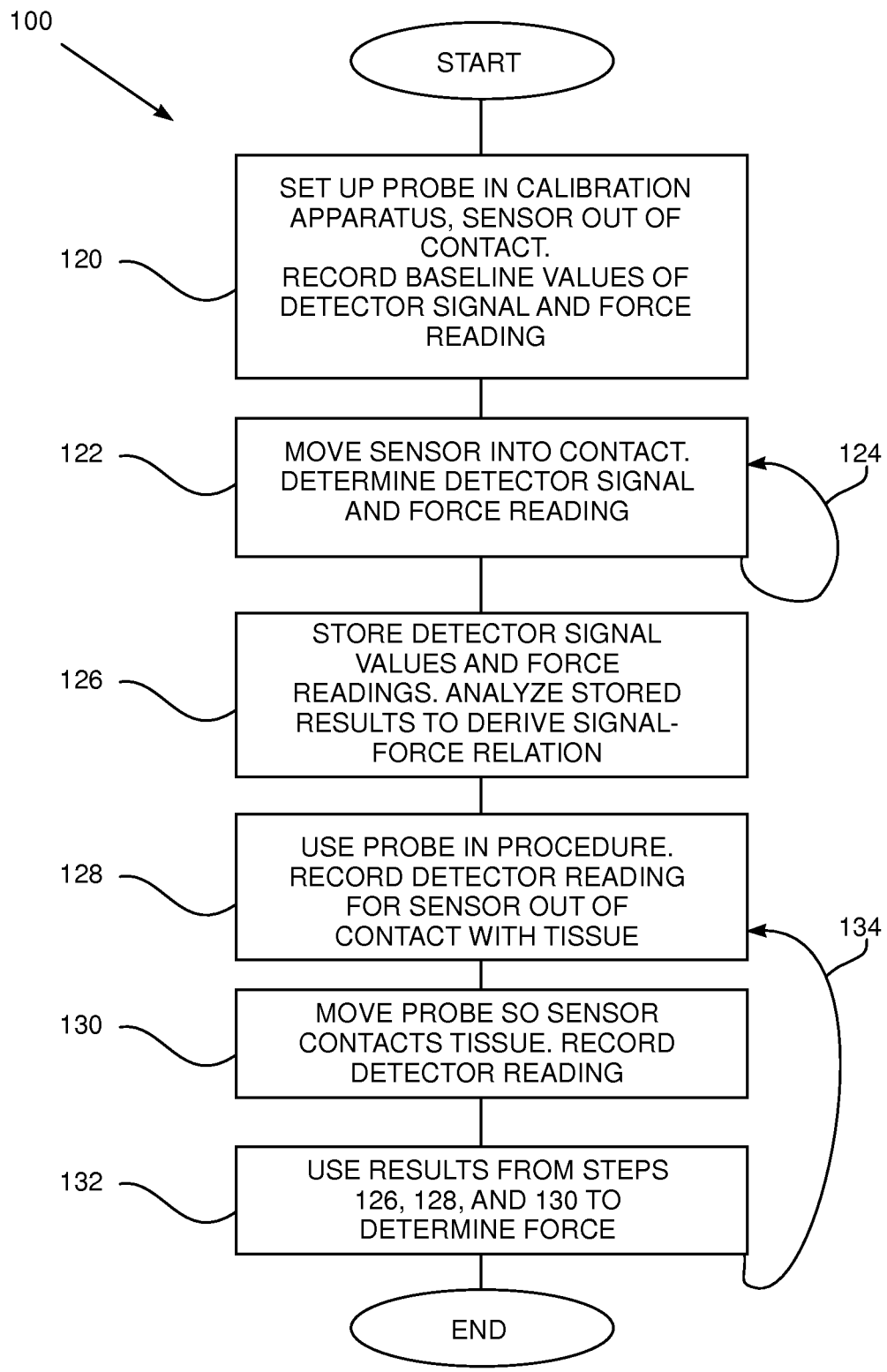
FIG. 5 is a flowchart of a process for calibrating and using the sensor, according to an embodiment of the present invention.
Figure 6:
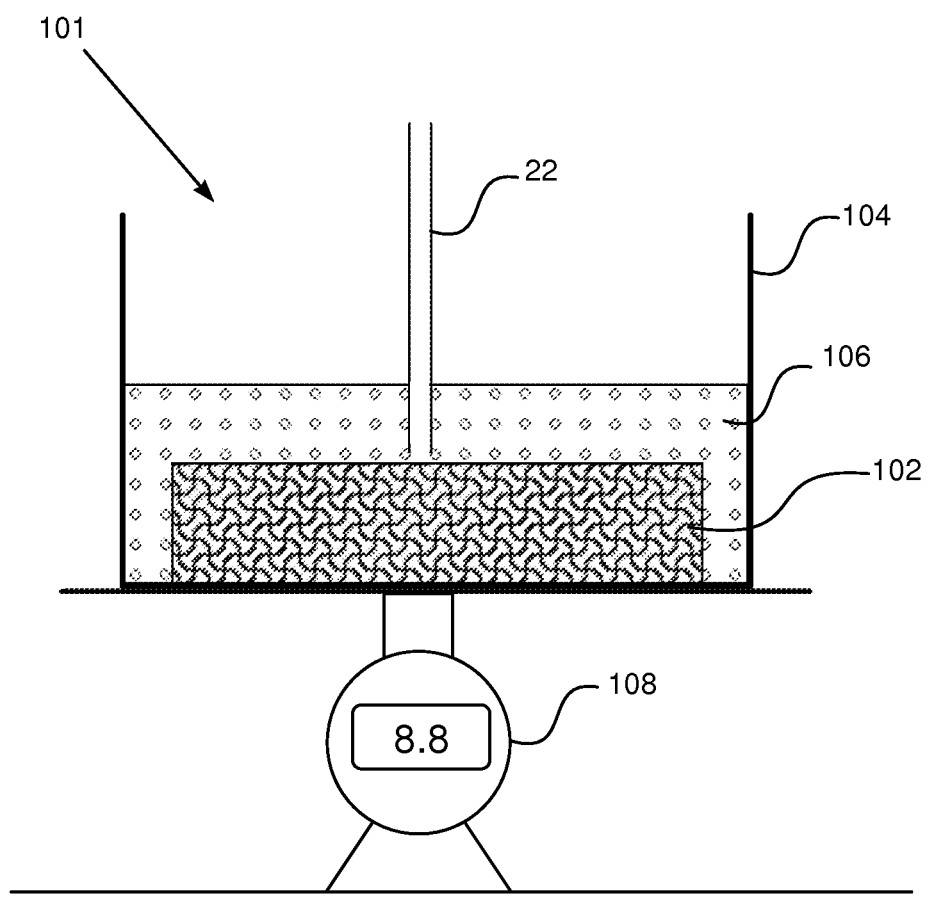
FIG. 6 is a schematic diagram of apparatus that may be used for the calibration part of the process of FIG. 5, according to an embodiment of the present invention.
Figure 7:
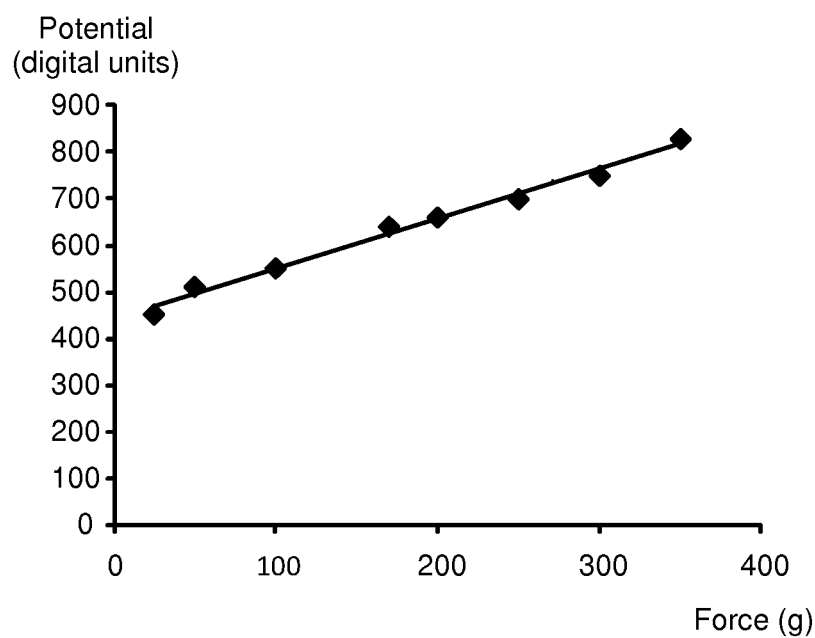
FIG. 7 is a schematic graph showing calibration results, according to an embodiment of the present invention.

FIG. 5 is a flowchart 100 of a process for calibrating and using sensor 32, FIG. 6 is a schematic diagram of apparatus 101 that may be used for the calibration part of the process, and FIG. 7 is a schematic graph showing calibration results, according to embodiments of the present invention. Sensor 32 is calibrated outside the body of patient 34 by determining the signal level from detector 74 for a variety of known effective forces applied to the sensor, the known forces typically including an effective force of zero. Methods for applying a known force may range from simply holding the probe, and its attached sensor, against a force meter such as a scale, to a system where the probe and its sensor are moved in a controlled manner against a force meter. The following description assumes calibration in a controlled manner, and other methods of calibration, and the appropriate adaptation of the description, will be apparent to those having ordinary skill in the art.

For the calibration, simulated body tissue 102 may be placed in a container 104, typically with a fluid 106 simulating blood covering the tissue. Alternatively, the calibration may be performed with no simulated tissue or fluid in container 104. The container and its contents are coupled to a force meter 108. Advantageously, measurements made by the force meter, as well as other measurement taken during the calibration of the sensor, are recorded by processor 34, which then analyzes the measurements. For simplicity, mounting equipment, as well as cabling or other connections between calibration apparatus 101 and the processor, is not shown in FIG. 6.

In a first step 120 of the calibration procedure, probe 22 is positioned so that it is in fluid 106 but so that sensor 32 is not in contact with tissue 102. Processor 34 activates source 64, and records the signal level of detector 74. In addition the processor records the force registered by meter 108. In this situation, i.e., with no contact between the sensor and the tissue, the detector signal level and the registered force, correspond to baseline values of the signal and the force.

In a force step 122, sensor 32 is moved so as to contact tissue 102, so that surface 72 deforms, i.e., the curvature of the surface decreases. The processor records the signal level of the detector, and the force registered by the force meter.

As shown by an arrow 124, step 122 is repeated. At each repetition, the probe is moved to a different position in tissue 102, so that the sensor exerts a different force on the tissue. For each different position, the processor records the signal level of the detector, and the force registered by the force meter.

In a results and analysis step 126, the processor stores the pairs of detector signals and force measurements, recorded in steps 122 and 124, as lookup table 54 in memory 38 (FIG. 1). The processor may analyze the stored results to generate calibration relation 52 between the detector signals and the measured forces, typically by analyzing the changes in signals and forces from the baseline values measured in step 120. The relation may be in any convenient form known in the art, such as a further lookup table (based on the values in table 54) or an equation relating the signals and the forces.

Steps 120-126 constitute procedures for calibrating sensor 32. FIG. 7 is an exemplary schematic graph of potential (in digital units) vs. force (in grams), determined in calibrating the sensor according to the above steps when the sensor is at the distal tip of a lasso probe. Typically, as illustrated by the graph, the relation between the force and the potential is substantially linear. Thus the ratio between the change of force applied to the sensor and the corresponding change of potential registered by the detector is constant. In the embodiment exemplified by the graph of FIG. 7, sensor 32 is able to measure forces between 0 g and approximately 400 g.

For simplicity, in the calibration process it may be assumed that source 64 delivers a constant radiation flux. However, source 64 is operated by processor 34, and there is no requirement that the radiation from source 64 is constant. Thus, in some embodiments, processor 34 is able to vary the level of radiation from source 64 dynamically, both during calibration and in subsequent procedure measurements. Such a variation enables the sensor to be calibrated for, and measure, a larger range of forces compared to a non-dynamic system. The process of operating sensor 32 dynamically and/or non-dynamically, and for formulating relation 52 for both cases, will be apparent to those having ordinary skill in the art.

In an initiate procedure step 128, probe 22 is used in the medical procedure described above, and is inserted so that distal tip 28 of the probe, comprising sensor 32, is close to but out of contact with body tissue 31. The positioning of the distal tip relative to tissue 31 may be determined by the tracking elements in the tip. Alternatively or additionally, a region where sensor 32 is not in contact with tissue 31 may be located by processor 34 determining that there is no significant change in the signal from detector 74, over a period of at least one heart cycle. U.S. patent application Ser. No. 12/938,458, which is assigned to the assignee of the present invention and which is incorporated herein by reference, describes force sensor measurements that are made in such a non-contact region.

Once the distal tip is in a non-contact region, processor 34 records a signal value of detector 74. The processor typically uses the recorded value to adjust for any "baseline drift" of sensor 32, as is described in application Ser. No. 12/938,458.

In a measurement step 130, probe 22 is moved until it contacts tissue 31, and the processor records the value of the signal from detector 74.

In a force determination step 132, the processor compares the relation determined in step 126, the baseline drift value recorded in step 128, and the measured detector value from step 130 to derive a value of the force on sensor 32. The comparison typically uses the change in detector values, from the value determined in step 128, to derive the force. Typically, as shown by an arrow 134, the processor repeats steps 128, 130, and 132 while moving distal tip 28 to different regions of tissue 31, so as to measure the forces experienced by sensor 32 when it contacts the different regions.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

I claim:

1. Sensing apparatus, comprising:
   a tubular catheter probe having a tubing wall, a proximal end and a distal end terminating in a distal tip, the distal tip being cylindrically shaped with an open distal end, and having an axis of symmetry,
   a sensor mounted within the distal tip, the sensor comprising a transparent, solid medium having a proximal surface and an elastic, distal outer surface, the elastic, distal outer surface being configured to contact a tissue within a living body and to deform in response to a force exerted by the body tissue on the distal outer surface;
   a radiation source contained within the tubing wall and coupled to the proximal surface of the transparent solid medium, the radiation source being configured to direct radiation through the transparent solid medium toward the distal outer surface;
   a radiation detector contained within the tubing wall and coupled to the proximal surface of the transparent solid medium, the radiation detector being configured to sense the radiation that is reflected from the distal outer surface and to output a signal indicative of an amplitude of the reflected radiation; and a processor, which is operatively coupled to the radiation source and the radiation detector and configured to measure a change in the signal due to deformation of the surface and, responsively to the change, to output an indication of the force.

2. The apparatus according to claim 1, wherein the radiation source is fixedly mounted on the proximal surface.

3. The apparatus according to claim 1, and comprising a radiation guide which couples the radiation source to the proximal surface.

4. The apparatus according to claim 1, wherein the radiation detector is fixedly mounted on the proximal surface.

5. The apparatus according to claim 1, and comprising a radiation guide which couples the radiation detector to the proximal surface.

6. The apparatus according to claim 1, wherein the medium has an axis of symmetry that is congruent with the axis of symmetry of the distal tip.

7. The apparatus according to claim 1, wherein the elastic, transparent outer surface is convex.

8. The apparatus according to claim 1, wherein the processor comprises a memory storing a calibration relation between the force and the change in the signal, and wherein the processor is configured to compare a further change in the signal with the calibration relation to output a value of a further force exerted by the body tissue on the surface.

9. Sensing apparatus, comprising:

a cylindrically shaped elastic transparent, solid medium having a proximal end, a distal end, and an axis of symmetry, the medium including a first outer surface on the distal end configured to contact a tissue within a living body and to deform in response to a force exerted by the tissue on the first outer surface;

a radiation source mounted directly to a second outer surface on the proximal end of the medium and configured to direct radiation toward the first outer surface, the second outer surface being opposite the first outer surface in a direction along the axis of symmetry;

a radiation detector mounted directly to the second outer surface of the medium and configured to sense the radiation that is reflected from the first outer surface and to output a signal indicative of an amplitude of the reflected radiation; and a processor, which is operatively coupled to the radiation source and the radiation detector and configured to measure a change in the signal due to deformation of the first outer surface and, responsively to the change, to output an indication of the force.

10. The apparatus according to claim 9, wherein the radiation source is fixedly mounted on the second outer surface.

11. The apparatus according to claim 9, wherein the radiation detector is fixedly mounted on the second outer surface.

12. The apparatus according to claim 9, and comprising a radiation guide which couples the radiation source to the second outer surface.

13. The apparatus according to claim 9, and comprising a radiation guide which couples the radiation detector to the second outer surface.

* * * * *